United States Patent [19]

Blake

[11] Patent Number: 4,465,481
[45] Date of Patent: Aug. 14, 1984

[54] SINGLE PIECE WOUND DRAIN CATHETER

[75] Inventor: Larry W. Blake, Costa Mesa, Calif.

[73] Assignee: Innovative Surgical Products, Inc., Santa Ana, Calif.

[21] Appl. No.: 371,941

[22] Filed: Apr. 26, 1982

Related U.S. Application Data

[63] Continuation-in-part of Ser. No. 238,640, Feb. 26, 1981, Pat. No. 4,398,910.

[51] Int. Cl.$^3$ ............................................. A61M 25/00
[52] U.S. Cl. ....................................... 604/280; 604/43
[58] Field of Search ..................... 604/93, 43, 280-284

[56] References Cited

U.S. PATENT DOCUMENTS

| | | | |
|---|---|---|---|
| 1,596,754 | 8/1926 | Moschelle | 604/282 |
| 1,879,249 | 9/1932 | Honsaker | 604/280 X |
| 2,134,152 | 10/1938 | Schwarzmayr | 604/93 |
| 2,450,217 | 9/1948 | Alcorn | 604/93 |
| 3,260,258 | 7/1966 | Berman | 604/93 X |
| 3,630,206 | 12/1971 | Gingold | 604/102 |
| 3,630,207 | 12/1971 | Kahn et al. | 604/282 |
| 4,307,723 | 12/1981 | Finney | 604/8 |
| 4,398,910 | 8/1983 | Blake et al. | 604/93 |

FOREIGN PATENT DOCUMENTS 105038 3/1917 United Kingdom ................. 604/93

OTHER PUBLICATIONS

Amer. Cyst. Makers Incorp. Catalogue, 1938, pp. 19, 37, (Hendrickson Drain).

*Primary Examiner*—Dalton L. Truluck
*Attorney, Agent, or Firm*—Knobbe, Martens, Olson & Bear

[57] ABSTRACT

The present invention comprises both a single piece wound drain catheter and the die from which such a catheter is extruded. The wound drain catheter of the present invention comprises a single, continuous flexible elongate member having a drain segment, a transition tube segment, and an extrusion tube segment. The drain segment comprises a fluted body having one or more longitudinal lumens in fluid communication with the wound in which the drain segment is located. The transition tube segment has internal cavities opening at one end into the lumens of the drain segment and at the other end into the central longitudinal cavity of the tubular extension tube segment. At least a portion of the drain segment is formed of a radiopaque material. The extension tube segment is formed of a translucent material, as is the outer portion of the transition segment. The entire flexible member is preferably made from a silicone elastomer having sufficient elasticity to permit the cross-sectional area of the member to decrease by at least 30% when a pulling force is applied to it. The die of the present invention, which is used to make the catheter of the present invention, comprises a die nozzle with a die cavity, within which are one or more die forms or die mandrels. These die forms and die mandrels are movable within the die cavity while the drain catheter of the present invention is being extruded to change the cross section of the extruded parison, so the single piece drain catheter of the present invention can be formed in a single continuous extrusion process. Consideration of the various aspects of the drain and die of the present invention will reveal that the apparatus of the present invention may be used in a variety of settings other than the draining of bodily wounds.

14 Claims, 31 Drawing Figures

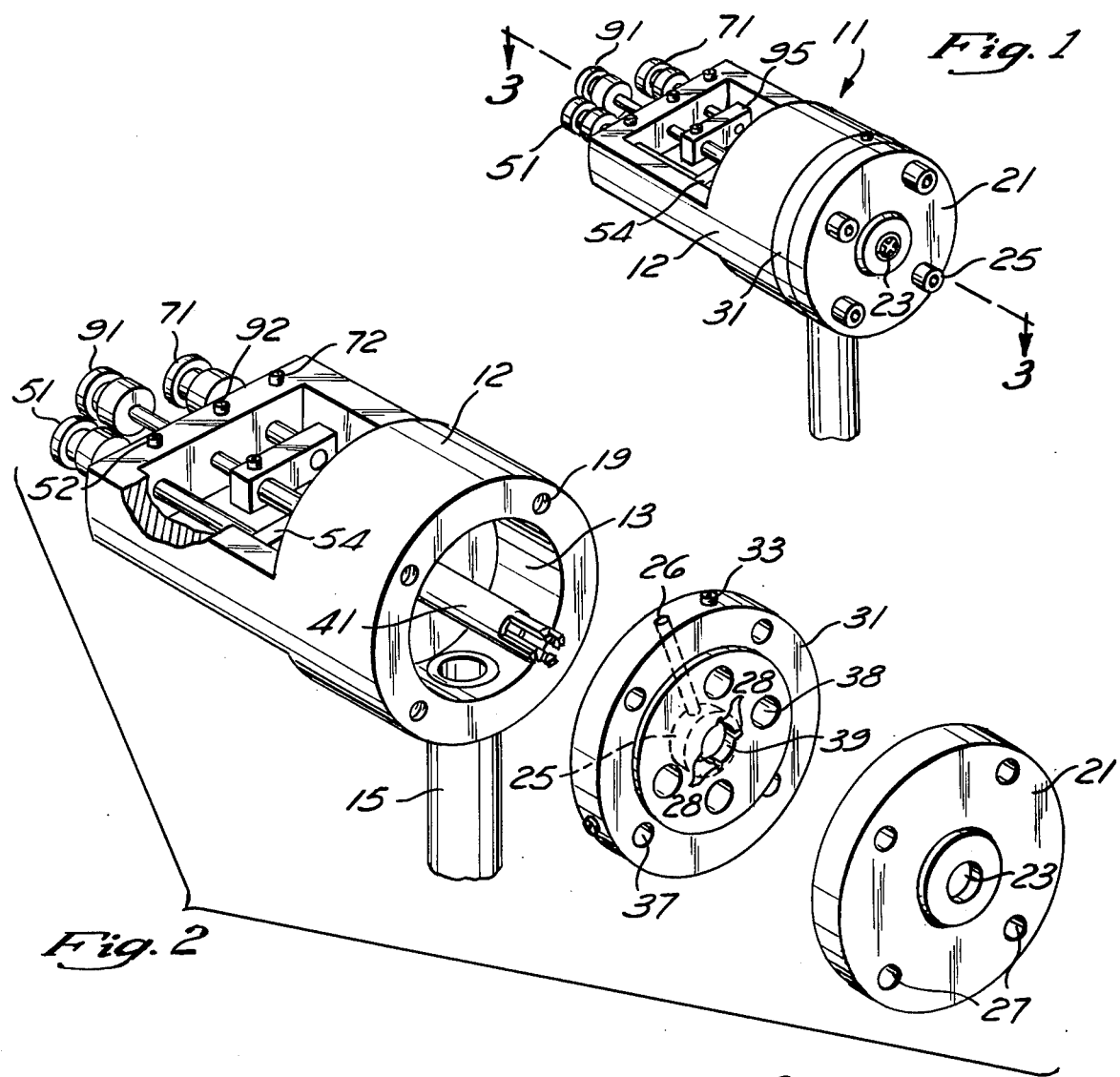
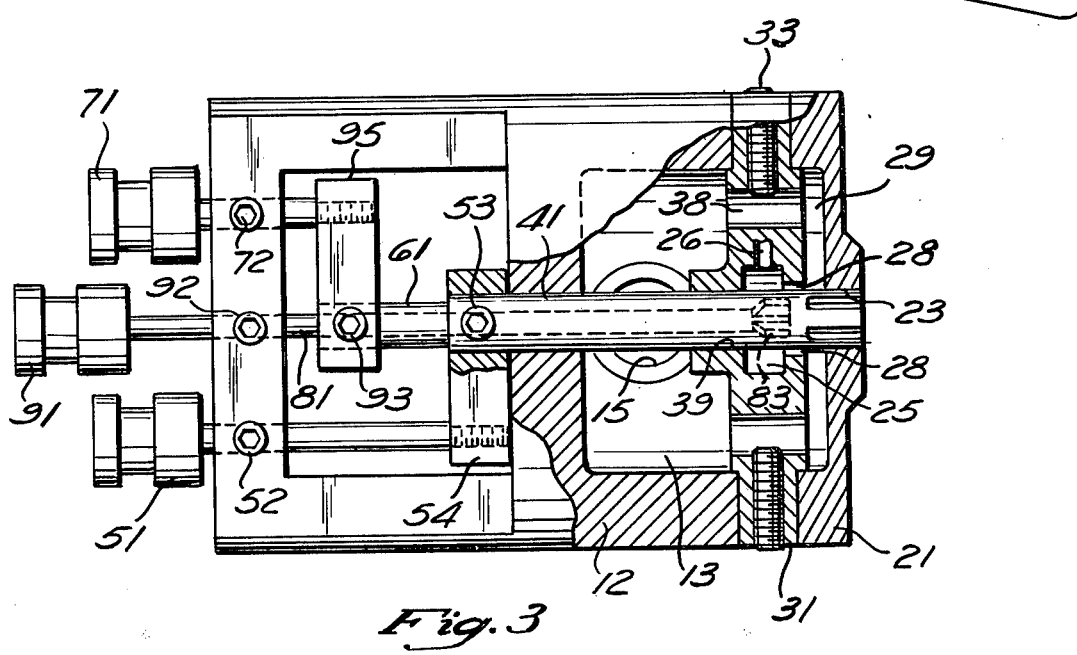

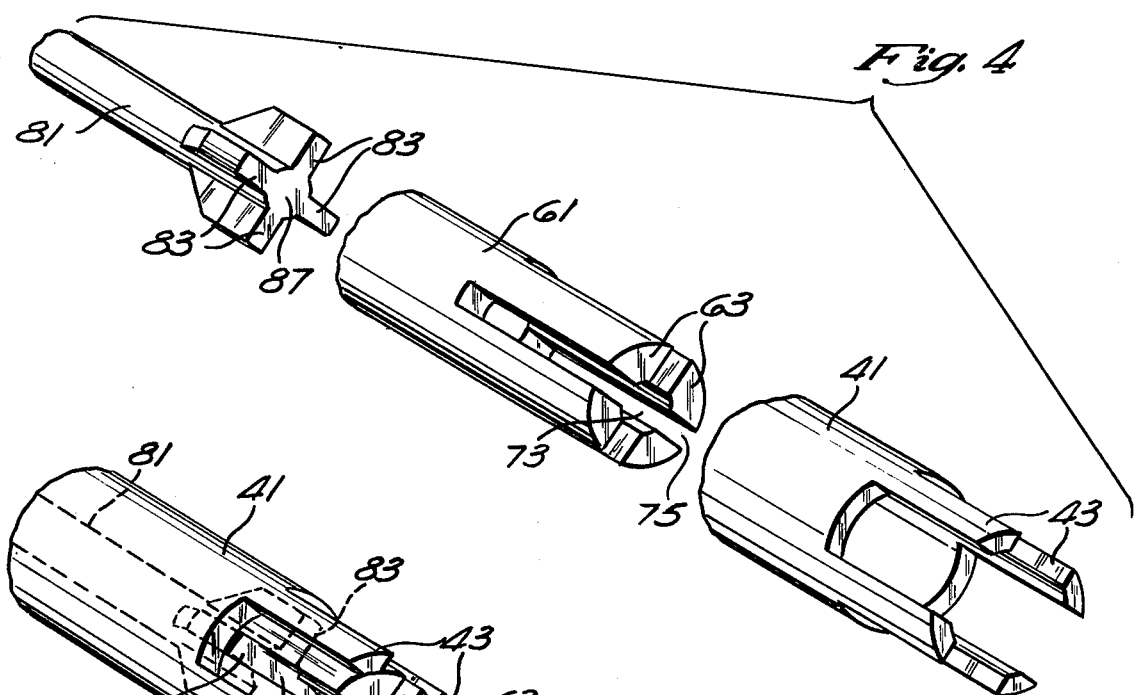
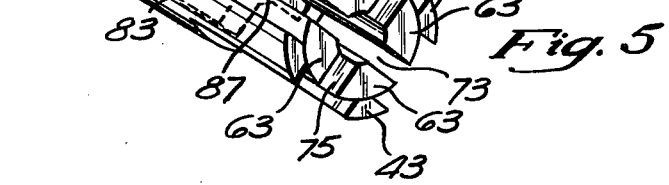
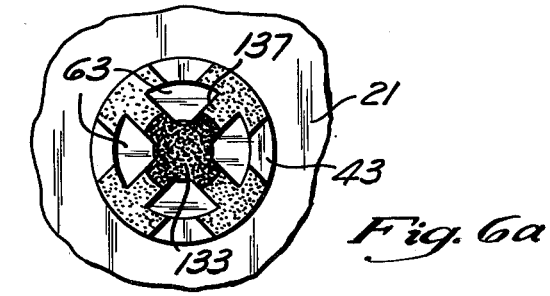
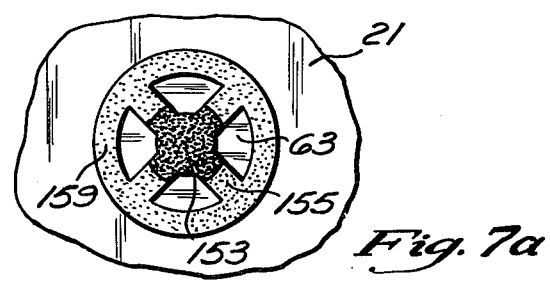

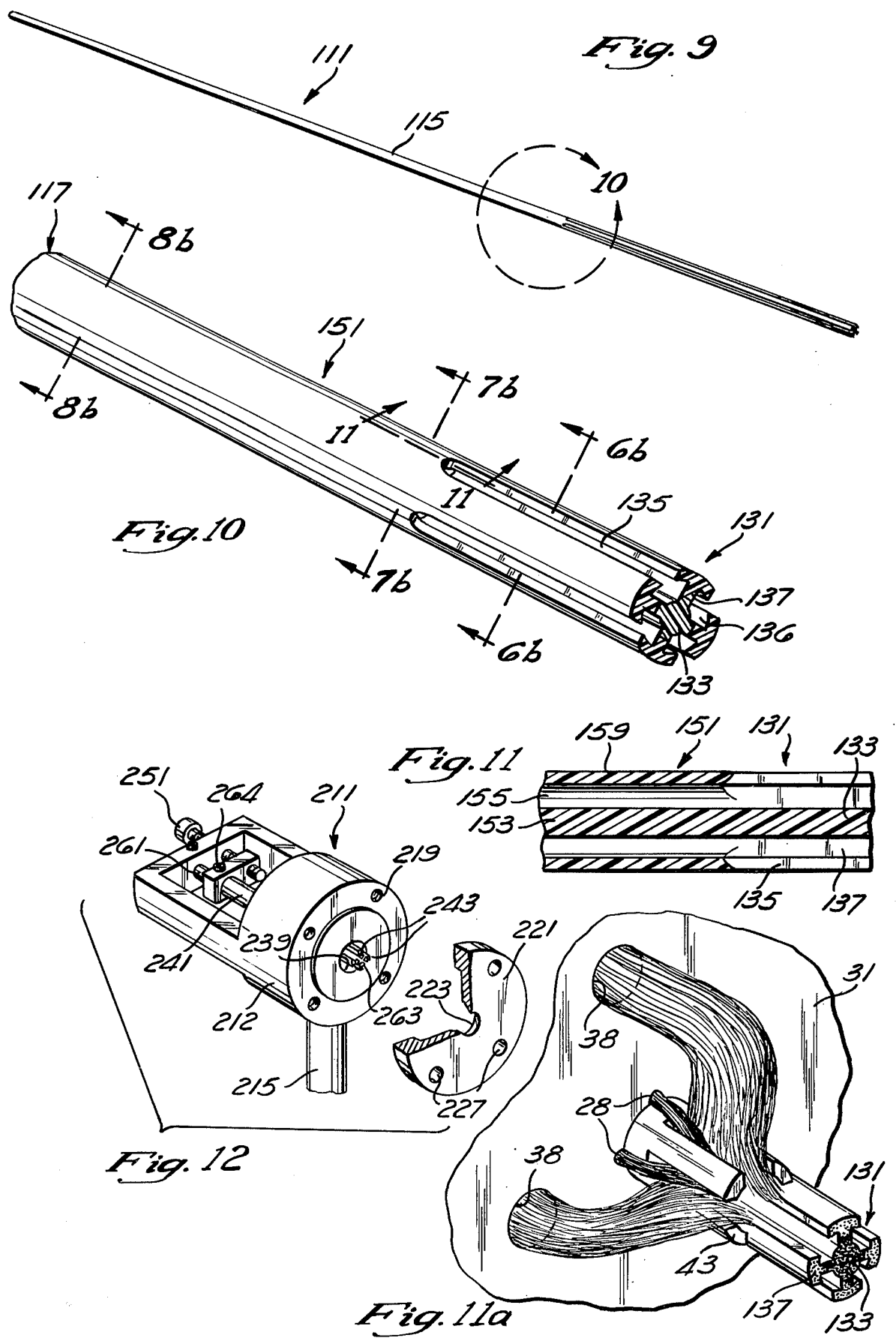

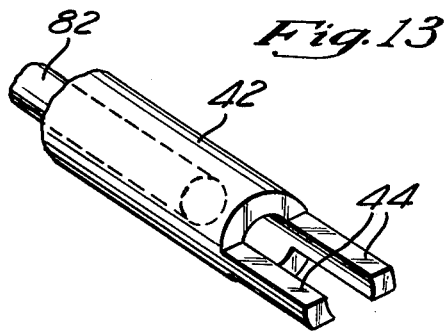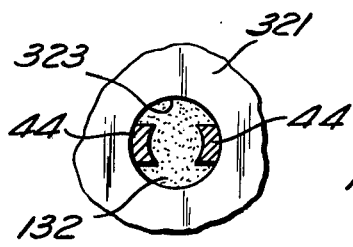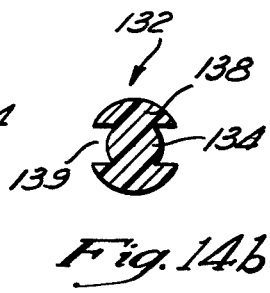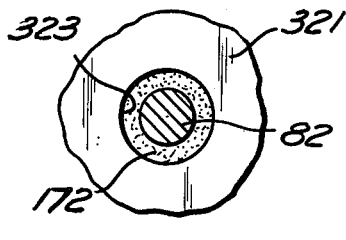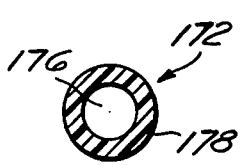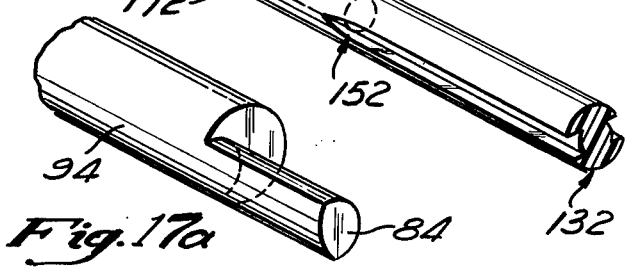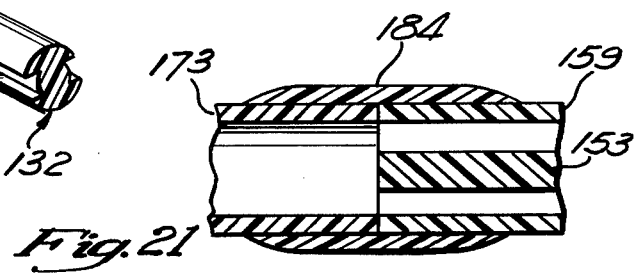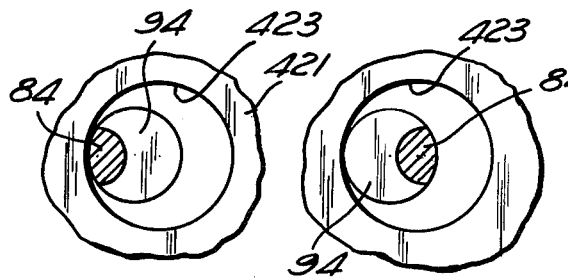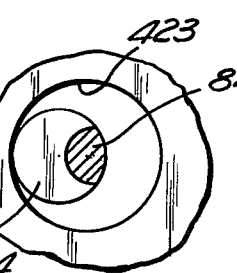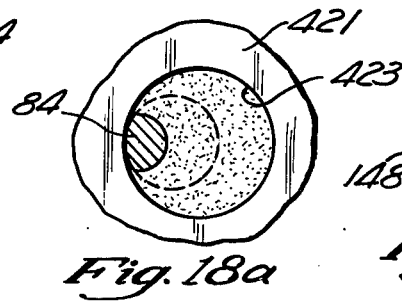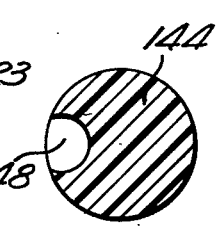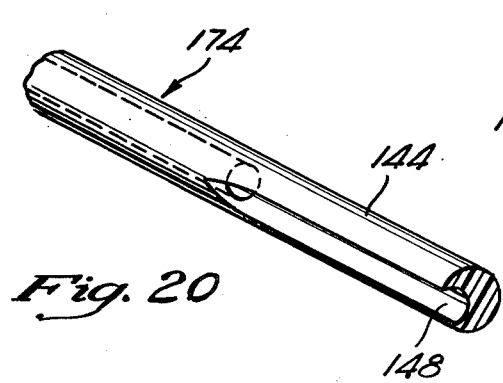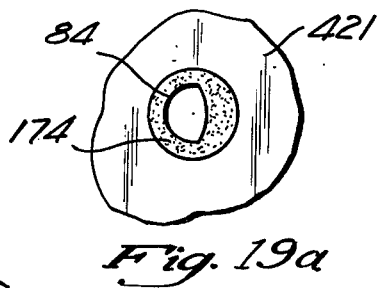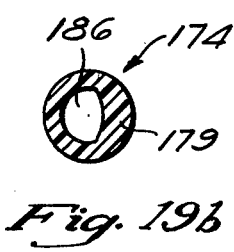

SINGLE PIECE WOUND DRAIN CATHETER

RELATED APPLICATIONS

This application is a continuation-in-part of application Ser. No. 238,640 filed Feb. 26, 1981, now U.S. Pat. No. 4,398,910.

BACKGROUND OF THE INVENTION

The present invention relates to wound drain catheters for draining fluid from, or supplying medication to, a wound.

Virtually all wound drain catheters presently used in closed wounds comprise a drain section for fluid communication with the wound and a separate outflow or extension tube section for carrying the fluid between the drain section and a reservoir. Typically, the drain section of a wound drain catheter comprises a length of tubing that is perforated by forming small apertures through the tubing wall. Several problems accompany this type of structure for the drain portion of the wound drain catheter. These problems are discussed in applicant's co-pending application, Ser. No. 238,640, filed Feb. 26, 1981. In that application a new type of drain section for a wound drain catheter is disclosed. This new type of drain section is formed of a silicone elastomer and comprises a fluted main body having longitudinal lumens open to the wound surrounding the drain portion. The advantages of a drain of this design over the drains of the prior art include an increased lumenal flow drainage area, elimination of stress points in the drain section that may lead to breakage of the drain as it is removed from the patient's body, and reduction of the risk that tissue growth will inhibit removal of drain.

Nevertheless, the drain portion there disclosed must be attached to a separate outflow tube. A butt joint is formed between the ends of the drain and the tube, with the two portions connected by an exterior collar. To ensure that the collar does not close the ends of the lumens of the drain portion, prohibiting fluid flow from the drain to the outflow tube, the end of the drain portion is undercut to provide a semi-spherical recess for fluid communication between the lumens and the outflow tube. This joint between the drain portion and the outflow tube establishes a point at which the strength of the drain catheter might be reduced, thus creating the possibility of breakage during removal of the drain from the patient's body. The collar, which necessarily has an outer diameter larger than the diameter of the drain portion and the extension tube portion, may provide added resistance to removal of the catheter. Although the possibility of this collar binding on material as it is pulled through the body is remote, the segment of increased diameter may give rise to added friction between the drain and the flesh surrounding it as the drain is pulled out of the body. In addition, forming the semi-spherical recess in the drain portion and attaching the drain portion to the outflow tube require additional steps during the manufacture of the catheter, making manufacture more time-consuming and expensive than the manufacture of a single piece catheter in a single process. Thus, while the drain catheter disclosed in patent application Ser. No. 238,640 substantially improved upon the prior art, room for further improvement remained.

The dies presently used in the extrusion of silicone or plastic materials comprise a die nozzle having a die cavity from which a parison is extruded. The die cavity has fixed within it die forms and/or die mandrels, around which the material flows as it is extruded from the die cavity to form a parison of the desired shape. Most of the die forms and die mandrels of the dies presently in use are fixed in place within the die cavity during the extrusion process. A few devices have a central die mandrel that has limited linear movement to vary the wall thickness of a tubular parison. But, to change the shape of the parison, the extrusion process must be halted, the dies moved or changed, and the extrusion process begun again. Consequently, changes of the parison shape are not possible in a single, continuous parison, so the parison extruded during a single extrusion is necessarily of uniform cross section. This limitation on the extrusion process has required the separate manufacture of the drain section and the extension tube section of wound drain catheters. In particular, with reference to applicant's co-pending application Ser. No. 238,640, the fluted drain section and the extension tube section of the wound drain catheter therein disclosed have necessarily been formed as separate pieces and joined together in a later process.

SUMMARY OF THE INVENTION

The present invention comprises a wound drain catheter formed of a single continuous elongate member of silicone material and the die for making such a catheter. The wound drain catheter of the present invention incorporates into a single member a drain segment, a transition tube segment, and an extension tube segment. The drain segment of the present invention comprises a fluted body with one or more longitudinal lumens, each open to the wound surrounding the drain segment. The transition tube segment allows fluid to flow from the lumens of the drain segment to the tubular extension tube segment. The end of the extension tube segment is connected to a reservoir for collecting or supplying fluid.

The drain segment of the preferred embodiment of the catheter of the present invention incorporates the design of the drain section of the wound drain catheter of applicant's co-pending application Ser. No. 238,640, filed Feb. 26, 1981. The drain section therein disclosed comprises a central core with strut portions projecting radially therefrom. An overhang portion is provided at the end of each of the strut portions, thereby forming "T"-shaped members. The overhang portions and strut portions cooperate to form channels or lumens extending throughout the length of the drain portion, each of which is open to the wound.

In the preferred embodiment of the invention, the drain segment is formed as part of a single unit with a transition tube segment comprising a central core with strut portions projecting radially therefrom and a tubular portion connected on its inner surface with the outer ends of the strut portions, so the tubular portion and the strut portions cooperate to define enclosed longitudinal channels in the transition tube segment. The strut portions of the transition tube segment are colinear with the strut portions of the drain segment so fluid flowing through each of the lumens of the drain segment flows into one of the channels of the transition tube segment.

The single unit drain catheter of the present invention also includes an extension tube segment comprising a tubular portion defining a central longitudinal cavity. One end of this segment is in fluid communication with all of the channels of the transition tube segment. The other end of the extension tube segment is connected to the reservoir.

In this preferred embodiment of the catheter, the elongate member is preferably formed of two materials extruded as a single unit. A first material, which is translucent, forms the tubular portion of the extension tube segment and the tubular portion of the transition tube segment. A second material, which is radiopaque, forms the core portion of the drain segment and the core portion of the transition tube segment.

Also disclosed herein are embodiments of the catheter of the present invention having smaller diameters than the diameter of the drain of the first embodiment. These smaller drains are suitable for smaller wounds requiring less fluid drainage.

In the first of these smaller drains, the drain segment comprises a core portion with two curved outer portions formed on opposite sides of the core portion. Each of these outer portions encircles less than one-half the circumference of the core portion, defining two longitudinal lumens between them. The transition tube segment of this embodiment comprises two separate outer curved portions that are extensions of the outer curved portions of the drain segment, defining diametrically between them a central longitudinal cavity that is continuous with the cavity of the extension tube segment and defining circumferentially between them two channels that are continuous with the lumens of the drain segment, the channels communicating along their lengths with the central opening. The tubular extension tube segment of this embodiment is formed as a single unit with the transition tube segment and the drain segment.

In the third embodiment of the catheter of the present invention, a single longitudinal lumen is provided in the drain segment. The drain segment comprises a substantially cylindrical body with a groove formed in the outer surface. The transition tube segment of this embodiment is also formed as a single unit with the drain segment and comprises an enclosed channel in fluid communication at one end with the single longitudinal lumen of the drain segment and at the other end with the longitudinal cavity of the extension tube segment.

The drain segment of the catheter of any of the above-described embodiments is preferably formed at least partially of radiopaque material, while the extension segment is formed of translucent material.

In any of the above-described embodiments, the drain of the invention is formed of a silicone elastomer having substantial tensile strength and elasticity. As mentioned above, forming the entire wound drain catheter as a single unit eliminates the joint previously necessary between the drain section and the extension tube section, thus eliminating the collar holding the two sections together. The external diameter of the catheter remains virtually constant throughout its length, with no collar of diameter greater than the diameter of the catheter present to provide resistance to removal of the drain from the patient's body. Also eliminated is the possibility of separation of the drain section from the extension tube section at the joint. In addition, forming the entire drain catheter unit from a silicone elastomer provides the transition tube segment and the extension tube segment with the reduction in cross sectional area capability previously found to be advantageous for the drain segment. This capability is beneficial because at least a portion of the transition tube segment, and possibly a portion of the extension tube segment, is within the patient's body when the drain segment is positioned in the closed, deep wound. Thus, providing a transition tube segment and extension tube segment that reduce in cross sectional area in response to a tensile force allows the drain of the present invention to be removed from the patient's body with a minimum of effort by the surgeon and a minimum of pain to the patient.

The present invention additionally comprises a die for making a single piece wound drain catheter, such as those just described. The die of the present invention includes die forms and die mandrels within the die cavity that can be moved between positions while the parison is being extruded to change the shape of the parison during a single extrusion process, permitting the formation of a single, continuous parison that has a cross section that is not uniform throughout its length. This permits the formation of the wound drain catheter of the present invention that comprises a single continuous elongate member incorporating a drain segment, a transition tube segment, and an extension tube segment.

In particular, the wound drain catheter of the first embodiment of the present invention may be formed by placing in the die cavity a first die form consisting of four prongs adjacent to the outer edge of the die cavity, a first die mandrel having a second die form on its end for forming the core portion and the projecting strut portions of the drain segment and the transition tube segment, and a second die mandrel that fills the second die form to form with the first die mandrel a cylindrical structure. The drain segment is formed by placing in the die cavity the first die form and the first die mandrel. The first die mandrel with the second die form on its end shapes the parison into the main body of the drain segment, while the prongs of the first die form create in the parison the longitudinal grooves that allow the lumens of the drain segment to communicate with the surrounding wound. To form the transition tube segment of the first embodiment of the catheter the first die form is removed from the die cavity while the extrusion process continues, which eliminates the grooves and provides the closed exterior surface defining the internal closed channels of the transition tube segment. The extension tube segment is then formed by sliding the inner die mandrel into the die form on the end of the first die mandrel to form a cylindrical die mandrel around which the tubular portion of the extension tube segment is formed.

Different embodiments of the die of the present invention are used to extrude the smaller drains of the present invention.

The drain having two lumens can be formed with a die having a linearly movable first die form consisting of two prongs adjacent the outer edge of the die cavity, forming in the parison the two lumens of the drain segment. As the first die form is withdrawn from the die cavity, a cylindrical die mandrel for forming in the parison the central cavity of the extension tube segment is brought into the die cavity. The very short transition tube segment is formed when both the first die form and the cylindrical die mandrel are simultaneously positioned in the die cavity for a brief time during the extrusion process.

To form the drain having a single lumen, a single die pin is provided in the die cavity. To form the drain segment of the catheter, this pin is positioned adjacent the edge of the die cavity, where the pin forms in the parison the single longitudinal lumen. As the extrusion process continues, the pin is moved toward the center of the die cavity, forming the transition tube segment. At the center of the die cavity the pin is a die mandrel around which the extension tube is formed.

Applicant has invented a new wound drain catheter comprising, in a single unit, a drain segment, a transition tube segment, and an extension tube segment. This wound drain catheter provides substantial advantages over those of the prior art, including increased lumenal flow drainage area, increased drain body cross sectional area, reduction of the possibility of breakage of the drain segment during removal, elimination of the possibility of rupture of the joint between the drain segment and the outflow tube segment, increased ease of removal of the drain from the patient's body, and reduced pain to the patient associated with removal of the drain.

Applicant's invention also comprises a new die useful for extruding the drain of the present invention and other products that are not uniform in cross section throughout their lengths. This die includes die forms and die mandrels in the die cavity that are movable during the extrusion process to alter the shape of the parison being extruded from the die. The die of the present invention is useful for the extrusion of a variety of products, including, but not limited to, the drain of the present invention.

BRIEF DESCRIPTION OF THE DRAWINGS

FIG. 1 is a perspective view of the die of the present invention.

FIG. 2 is an exploded perspective view of the die of the present invention.

FIG. 3 is a side cross sectional view of the assembled die of the present invention.

FIG. 4 is an exploded perspective view of the die form and die mandrels that fit in the die opening.

FIG. 5 is a perspective view of the die form and die mandrels assembled to fit in the die opening.

FIG. 6a is an end view of the die nozzle with the die mandrels and die form positioned to extrude the drain segment of the catheter.

FIG. 6b is a cross sectional view of the drain segment of the catheter, taken along line 6b—6b of FIG. 10.

FIG. 7a is an end view of the die nozzle with the die form and die mandrel positioned to extrude the transition tube segment of the catheter.

FIG. 7b is a cross sectional view of the transition tube segment of the catheter, taken along line 7b—7b of FIG. 10.

FIG. 8a is an end view of the die nozzle with the die form and die mandrels positioned to extrude the extension tube segment of the catheter.

FIG. 8b is a cross sectional view of the extension tube segment of the catheter, taken along line 8a—8b of FIG. 10.

FIG. 9 is a perspective view of the catheter of the present invention.

FIG. 10 is an enlarged perspective view of a portion of the catheter of FIG. 9.

FIG. 11 is a side cross sectional view of the catheter, taken along line 11—11 of FIG. 10.

FIG. 11a is a perspective view of the breaker plate of the die showing the flow of material being extruded.

FIG. 12 is an exploded perspective view of a first alternate embodiment of the die of the present invention.

FIG. 13 is a perspective view of the die form and die mandrel of a second alternate embodiment of the die.

FIG. 14a is an end view of the die nozzle of the second alternate embodiment of the die with the die form and die mandrel positioned to extrude the drain segment of a second alternate embodiment of the catheter.

FIG. 14b is a cross sectional view of the drain segment of the second alternate embodiment of the catheter.

FIG. 15a is an end view of the die nozzle of the second alternate embodiment of the die with the die form and die mandrel positioned to extrude the extension tube segment of the second alternate embodiment of the catheter.

FIG. 15b is a cross sectional view of the extension tube segment of the second alternate embodiment of the catheter.

FIG. 16 is a perspective view of the second alternate embodiment of the catheter.

FIG. 17a is a perspective view of the die mandrel of a third alternate embodiment of the die.

FIG. 17b is an end view of the die nozzle of the third alternate embodiment of the die with the die mandrel positioned to extrude the drain segment of a third alternate embodiment of the catheter.

FIG. 17c is an end view of the die nozzle of the third alternative embodiment of the die with the die mandrel positioned to extrude the extension tube segment of the third alternate embodiment of the catheter.

FIG. 18a is an end view of the die nozzle of the third alternate embodiment of the die with the die mandrel positioned to extrude the drain segment of the third alternate embodiment of the catheter.

FIG. 18b is a cross sectional view of the drain segment of the third alternate embodiment of the catheter.

FIG. 19a is an end view of the die nozzle of the third alternate embodiment of the die with the die mandrel positioned to extrude the extension tube segment of the third alternate embodiment of the catheter.

FIG. 19b is a cross sectional view of the extension tube segment of the third alternate embodiment of the catheter.

FIG. 20 is a perspective view of the third alternate embodiment of the catheter.

FIG. 21 is a side cross sectional view of the joint between the drain segment and the extension tube segment of a first alternate embodiment of the catheter.

DETAILED DESCRIPTION OF THE PREFERRED EMBODIMENT

The wound drain catheter and the extrusion die with which it is made are herein described in detail with reference to the accompanying drawings.

The Drain

Referring particularly to FIGS. 9 and 10, the preferred embodiment of the wound drain catheter 111 of the present invention is shown. The catheter 111 comprises a single continuous elongate member 115 comprising a drain segment 131, a second segment 151, called the transition tube segment, and a third segment 171, called the extension tube segment.

The cross section of drain segment 131 shown in FIG. 6b, shows the central core portion 133 with T-shaped members 137 projecting therefrom. T-shaped members 137 cooperate to form longitudinal flutes or lumens, comprising channels 136 communicating with the environment surrounding the drain through grooves 135. The drain segment 131 of the preferred embodiment is the same as the drain disclosed in applicant's U.S. patent application Ser. No. 238,640, filed Feb. 26, 1981. The core portion 133 is best formed of a radiopaque material. This permits the location of the drain segment 131 to appear in X-rays taken of the wound area. To present a large image in X-rays portions of the strut portions 137 are also formed of radiopaque material.

FIG. 7b shows the cross section of transition tube segment 151. Core portion 153 is colinear with the core portion 133 of the drain segment 131. Each of the strut portions 155 projecting from core portion 153 is colinear with one of the T-shaped portions 137 of the drain segment 131. The inner surface of tubular portion 159 is connected to the ends of the strut portions 155 so the tubular portion 159 and the strut portions 155 cooperate to form enclosed longitudinal channels 156. Each of the channels 156 communicates with one of the lumens 136 of the drain segment 131.

The core portion 153 of the transition tube segment 151 is advantageously formed of the radiopaque material of which the core portion 133 of the drain segment 131 is formed so it also will appear in X-rays of the patient. The tubular portion 159, however, is best formed of a translucent material so the doctor or nurse can view the flow of fluid through the channels 156.

The point of transition between the drain segment 131 and the transition tube segment 151 is shown in longitudinal cross section in FIG. 11. The central core portion 133 of the drain segment 131 continues into the central core portion 153 of the transition tube segment 151. The strut portions 155 and the tubular portion 159 of the transition tube segment 152 are continuations of T-shaped members 137 of the drain segment 131, with grooves 135 of the drain segment filled in.

Extension tube segment 171 is shown in cross section in FIG. 8b. Extension tube segment 171 comprises tubular portion 177 defining internal longitudinal cavity 175. Tubular portion 177 is a continuation of tubular portion 159 so that cavity 175 communicates with all of the channels 156 of the transition tube segment 151.

The tubular portion 177 of extension tube segment 171 is formed of translucent material so the doctor or nurse can view the flow of fluid through cavity 175. Since, when the catheter is in use, the extension tube segment 171 is not within the patient's body, it need not be constructed of a radiopaque material that will show up on X-rays.

The diameter of each of the drain segment 131, the transition tube segment 151, and the extension tube segment 171 are advantageously equal to one another, so the diameter of the elongate member 115 is constant throughout its length.

The Die

The preferred embodiment of the drain, described above, is extruded from the die 11 shown in FIGS. 1, 2, and 3. In FIG. 1 the die is shown as assembled for extruding a parison, with breaker plate 31 and die nozzle 21 attached to main body 12 by screws 25. Die cavity 23 is centrally located in nozzle 21.

Formed within the main body 12 of the die is first plenum 13 (FIG. 2). Sprue 15 communicates with this first plenum 13. Breaker plate 31 fits on the front of main body 12, completing the enclosure of plenum 13.

Breaker plate 31 has formed through it a central opening 39. Around the central opening 39, within the thickness of breaker plate 31, is annular second plenum 25. This annular second plenum 25 is surrounded on three sides by the breaker plate 31, while its fourth inner side, opens into central opening 39. Openings 28 around the perimeter of opening 39 communicate with second plenum 25. Additionally, sprue 26 communicates with second plenum 25.

Openings 38 through breaker plate 31 are placed so that they communicate with plenum 13 when breaker plate 31 is attached to the front of main body 12. An adjustment screw 33 is provided for each of the breaker plate openings 38. These screws 33 may be turned inwardly into or outwardly out of breaker plate openings 38 and adjustably block the opening 38. Additionally, screw holes 37 are provided through the breaker plate 31, which, when the die is assembled, align with screw holes 19 in the main body 12.

FIG. 3 shows the assembled die in cross-section, the view being from the top of the die opposite sprue 15. Sprue 15 communicates with first plenum 13. Sprue 26 communicates with second plenum 25, which is formed in breaker plate 31 around the central opening 39. Third plenum 29 is formed between breaker plate 31 and die nozzle 21. Breaker plate openings 38 provide communication between first plenum 13 and the third plenum 29. As noted above, adjustment screws 33 may be selectively moved into or out of openings 38 to adjustably block the flow through those openings.

Small openings 28 through the front part of breaker plate 31 provide communication between second plenum 25 and third plenum 29 when the die mandrel shafts 41, 61, and 81 are in place in the die assembly.

Cannular shaft 41, the end of which contains one of the die forms that fits into die opening 23, and which surrounds the other shaft containing the die forms and die mandrels of the die, is positioned through first plenum 13, central opening 39 in breaker plate 31, and terminates in die opening 23 of die nozzle 21. A second cannular shaft 61 fits in the central cavity of cannular shaft 41. Through the central cavity of cannular shaft 61 passes cylindrical shaft 81.

The outer ends of each of the shafts 41, 61, and 81 are shown in FIG. 4. The end of the cannular shaft 41 is a first die form comprising of prongs 43. Prongs 43 are shaped to slidingly engage the edge of die opening 23 when the first die form is positioned in the die cavity, and to slidingly engage the outer surface of the curved portions 63 at the end of cannular shaft 61.

The end of shaft 61 is a first die mandrel having on its end a second die form. This die mandrel includes curved outer portions or pins 63 surrounding central opening 73, the gaps between the pins defining radial openings 75. The number of curved outer portions 63 equals the number of prongs 43 on shaft 41.

The end of shaft 81 is a second die mandrel with a core portion 87 and projecting strut portions 83. The core portion 87 and the strut portions 83 fit into central opening 73 and radial openings 75 of the die form at the end of the first die mandrel on shaft 61.

The ends of shafts 41, 61, and 81 fit together as shown in FIG. 5. The inner surfaces of prongs 43 fit against the outer surfaces of curved portions 63 between the radial openings 75. Core portions 87 and strut portions 83 fit into openings 73 and 75.

Cannular shaft 41, with prongs 43 on its end, is linearly movable with respect to shaft 61, so the prongs 43 may be moved from the position adjacent the ends of curved portions 63, as shown in FIG. 5, to a position in which the ends of the prongs 43 are withdrawn from the ends of the curved portions 63. When the prongs 43 are in this latter position, a gap is formed between the outer surfaces of curved portions 63 and the edge of die cavity 23.

Shaft 81 is also linearly movable with respect to shaft 61, to permit core portion 87 and strut portions 83 to selectively fill the ends of openings 73 and 75 or be withdrawn from that position so openings 73 and 75 are open in the die cavity 23.

Referring again to FIG. 3, the ends of shafts 41, 61, and 81 away from die cavity 23 are fitted, respectively, with knobs 51, 71, and 91. Each of these knobs permits the control of the linear movement of one of the shafts 41, 61, and 81 so the end thereof may be selectively positioned either in die cavity 23 or withdrawn therefrom.

Set screws 53 and 93 permit blocks 54 and 95, into which are screwed the stems of knobs 51 and 71, to be locked in position relative to cannular shafts 41 and 61. The relative positions of the shafts 41 and 61 and the blocks 54 and 95 are adjusted until the proper range of movement of the shafts (with their attached prongs 43 and curved portions 63) with respect to each other and with respect to the main body 12 is obtained. Then set screws 53 and 93 are tightened through apertures in blocks 54 and 95 until they bear upon the shafts 41 and 61 to fix the relative positions of the blocks and shafts.

Set screws 52, 72, and 92 are provided to permit shafts 41, 61, and 81 to be locked in position relative to the main body 12. Set screw 52 can be screwed in to bear upon the stem of knob 51 to prevent the movement of shaft 41 relative to the main body 12 and the die nozzle 21. Set screw 72 can be screwed inward to bear upon the stem of knob 71 to prevent the movement of shaft 61 relative to main body 12. Set screw 92 can similarly be used to lock shaft 81 in position relative to main body 12.

Automatic control means, such as air cylinders controlled by a timing mechanism (not shown) are attached to knobs 51, 71, and 91 to control the movement of the shafts 41, 61, and 81, and their attached die form and die mandrels during the extrusion process.

Operation of the Die

The operation of the preferred embodiment of the die of the present invention will be explained. Referring to FIG. 3, a molten material suitable for extruding into a drain of the present invention, preferrably a translucent silicone material, flows through sprue 15 into first plenum 13 in main body 12. The first material then flows through openings 38 in the breaker plate 31 into third plenum 29. The flow through each opening 38 is adjusted by means of adjustment screws 33 so the flow of the first material into third plenum 29 is approximately evenly distributed.

At the same time, a second extrudable material, which in the present invention is advantageously a radiopaque silicone material, flows through sprue 26 into annular second plenum 25. This second material then flows through openings 28 into third plenum 29.

Because of the pressure of the first material (which has entered third plenum 29 through openings 38), as the first material moves toward opening 23 in the die nozzle 21, it pushes the second material (which has entered the third plenum 29 through openings 28) toward the center of the die opening 23, as shown in FIG. 11a. In this way, the second material, which has flowed into the die through sprue 26, emerges in approximately the center of die opening 23 during the extrusion process, surrounded by the first material, which entered the die through sprue 15. As these materials are molten, and in most respects chemically identical, these two materials bond together as they are extruded in the same manner that silicone material ordinarily bonds to itself during the extrusion process. By varying the relative amounts of the first and second materials fed through sprues 15 and 26, different proportions of the first and second materials in the extruded parison may be obtained.

During normal operation, the end of shaft 61 is always positioned in die cavity 23 so curved portions 63 form a die mandrel in the die cavity 23.

When the prongs 43 of the first die form on the end of cannular shaft 41 are also placed in position in the die cavity 23 with the ends of curved portions 63, the die opening 23 looks as shown in FIG. 6a. This arrangement of the first die mandrel and the first die form produces an extrudate or parison of the drain segment 131 shown in FIG. 6b. The material being extruded flows through the central opening 73 and radial openings 75 (FIG. 5) between the curved portions 63, and around the outer surfaces of the curved portions 63 to form "T"-shaped members 137, with prongs 43 forming grooves 135 in the extrudate.

The formation of the drain segment 131 is best carried out by feeding a translucent material through sprue 15 and a radiopaque material through sprue 26. As discussed above, the material fed through sprue 15 presses the material fed through sprue 26 into second plenum 25 toward the center of the die opening 23 as the two materials are extruded together. This will yield a central core portion (in this case core portion 133) of radiopaque material and outer portions of translucent material. Alternately, during the extrusion of the drain segment 131, the translucent material flow through sprue 15 may be halted so that the entire drain segment body is formed of the radiopaque material flowing through sprue 26. Virtually any proportion of the two materials may be extruded through die opening 23 by varying the rates of flow through sprues 15 and 26. In any case, the radiopaque material permits the catheter to appear on x-rays of the patient's wound area.

With just the first die mandrel with curved portions 63 positioned in the die cavity 23 and the prongs 43 withdrawn, the die cavity 23 looks as shown in FIG. 7a. As the material flows through the die cavity 23 it is formed into the transition tube segment 151 shown in cross section in FIG. 7b. The material being extruded flows through the central opening 73 and radial openings 75 and the outer surfaces of around curved portions 63 to form core portion 153, strut portions 155 and tubular portion 159.

During the extrusion of the transition tube segment, if the translucent first material is fed through sprue 15 and the radiopaque material through sprue 26, a transition tube segment 151 may be formed with a radiopaque core portion 153 (FIG. 7b) and a translucent tubular outer portion 159. Varying the proportion of the materials fed through the two sprues permits control of the relative proportions of the transition tube segment that is translucent or radiopaque. For example, feeding a larger amount of radiopaque material through sprue 26 will result in a larger portion of the strut portions 155 being formed of the radiopaque material, and less of the strut portions 155 being formed of the translucent material.

With the prongs 43 withdrawn from the die cavity 23 and the second die mandrel on the end of shaft 81 positioned in the die cavity so the core portion 87 and strut portions 83 fill the central and radial openings 73 and 75, the die cavity 23 looks as shown in FIG. 8a and a tubular extrudate in the shape of the extension tube segment shown in FIG. 8b is produced.

During the extrusion of the extension tube segment 171, the flow of radiopaque material through sprue 26 is closed off, so that the tubular portion 177 is formed entirely of translucent material. The translucent tubular portion 177 allows the doctor or nurse to view the flow of fluid through the catheter, so he or she can determine if proper healing is taking place. Since the extension tube segment will be external to the patient's body, it is unimportant whether this portion of the catheter be visible on x-rays. If the flow of radiopaque material through sprue 26 is continued during extrusion of the extension tube segment 171, the radiopaque material will be forced toward the center of the die opening 23, which would result in the radiopaque material being extruded around the perimeter of the outer surface of the die pins 63 and the ends of strut portion 83, which would give tubular portion 177 a very thin layer of radiopaque material on its inner surface.

Selectively moving knobs 51 and 91 while the extrusion process continues, to move the prongs 43 of the first die form and the core portion 87 and radial portions 83 of the second die mandrel into position in the die cavity 23 and withdrawn therefrom changes the shape of the extrudate without stopping the extrusion process. In this way, a single continuous member of extruded material comprising a drain segment 131, a transition tube segment 151, and an extension tube segment 171 may be formed. First, the drain segment is formed by placing the prongs 43 in the die cavity 23 as shown in FIG. 6a; then the transition tube segment is formed by withdrawing the prongs 43, as shown in FIG. 7a; and then the extension tube segment is formed by placing portions 87 and 83 in the opening with curved pins 63, as shown in FIG. 8a. This may be repeated without halting the extrusion process, with the individual catheters cut apart in a separate action.

During the extrusion process, the relative amounts of material flowing through sprues 15 and 26 are carefully controlled to ensure proper extrusion. During extrusion of the drain segment 131, sprue 26 is opened to permit radiopaque material to flow through the sprue 26 into second plenum 25. Generally, sprue 15 will also be kept open so the translucent material will also flow into and through the die. At the conclusion of the extrusion of the drain segment 131, the flows through sprues 15 and 26 are adjusted so that as the transition tube segment 151 is extruded, a proper relationship between the amount of radiopaque material and the amount of translucent material is maintained. As the extrusion of the transition tube segment continues, the flow of material through sprue 26 is closed off until the parison is formed entirely of the translucent material fed through sprue 15. Then, as the parison is changed from the transition tube segment to the extension tube segment, the translucent material is all that is flowing through the die, and the extension tube segment 171 is formed entirely of the translucent material.

Use of the Catheter

To use the catheter of the present invention in a closed wound, a trocar is attached to the free end of the extension tube segment 171 and the elongate member 115 is drawn through the wound area and out of the body through the skin. When the radiopaque material in the transition tube segment 151 appears at the skin surface as the catheter is drawn out, the pulling is stopped, as this indicates the drain segment 131 is in position within the wound. The skin is then sealed around the elongate member. The skin is preferably sealed around the transition tube segment 151, rather than the extension tube segment 171, as the transition tube segment has greater rigidity and is less likely to be pinched closed when the skin is sealed around it. The trocar is disconnected from the end of the extension tube segment 171, and a fluid reservoir is connected to collect the fluid that flows from the wound.

When the catheter is to be removed, the reservoir is disconnected. A tensile force is applied to the elongate member, which causes the member to reduce in cross sectional area so the flesh surrounding the catheter relaxes its grip upon the drain and removal of the catheter is made easier. The advantages of the shape of the drain segment of the catheter are discussed in applicant's application Ser. No. 238,640. The single piece catheter of the present invention has the advantages of the fluted drain segment, plus the additional advantages of a continuous, one-piece member with a smooth exterior and simpler manufacturing. This smooth exterior has no protrusions, such as an external collar around a joint, that may bind on flesh or other material in the body during removal to make removal more difficult. Furthermore, since the entire catheter is made of the same material, the reduction in cross sectional area is approximately the same in the transition tube segment and in the drain segment. Consequently, the flesh surrounding the catheter along its entire length within the body relaxes its grip to make removal easier and less painful.

First Alternate Embodiment

A first alternate embodiment of the die of the present invention is shown in FIG. 12. There are two primary differences between this embodiment and the embodiment shown in FIG. 1. The first difference is that within the die opening 223 are only one die form 243 and one die mandrel 263, which has on its end a second die form. There is no second die mandrel to fill this second die form. The other primary difference is that there is only one internal plenum (not shown, but similar to plenum 13 of the first embodiment) which is within the main body 212.

Sprue 215 communicates between the internal plenum and a source of extrudable material. Opening 239 in the face of main body 212 provides an outlet for the material from the internal plenum. The opening 239 communicates directly with the die opening or cavity 223 in the die nozzle 221, with not intervening second plenum similar to plenum 29 of the first embodiment (FIG. 3). Openings 227 in the die nozzle 221 admit screws similar to screws 25 (FIG. 1), which screw into openings 219 on the face of the main body 212 to hold the die nozzle 221 securely to main body 212.

The die form 243 has the same shape as the end of shaft 41 of the principle embodiment and is linearly moveable within the die body 212. The die form 243 moves between a first position in which it is located within the die opening 223 and a second position in which it is withdrawn from the die opening into the die body 212.

The die mandrel 263 has the same shape as the end of shaft 61 of the principle embodiment and is also linearly movable between a first position in which its end is in the center of die cavity 223 and a second position in which the end is withdrawn into the main body 212. During normal operation of the die the die mandrel 263 remains in the first position in die cavity 223.

The cooperation of die form 243 and die mandrel 263 is the same as the cooperation of the prongs 43 of the first die form and the curved portions 63 of the first die mandrel of the preferred embodiment (FIG. 5). When the die form 243 is withdrawn from the die cavity 223 and the die mandrel 263 is in its first position in the die cavity 223, the die cavity 223 looks just as the die cavity 23 appears in FIG. 7a and extrudes an extrudate in the shape of the transition tube segment 151, as shown in FIG. 7b. When the first die form 243 is moved to its first position in the die cavity 223, the die nozzle 221 looks as the die nozzle 21 shown in FIG. 6a, and produces an extrudate in the shape of the drain segment 131, as shown in FIG. 6b.

Control knob 251 may be used to move cannular shaft 241, on the end of which is first die form 243. Set screw 264 may be used to lock cannular shaft 241 in position relative to shaft 261, the end of which contains die mandrel 263.

Operation of the First Alternative Embodiment

The operation of this first alternate embodiment of the present invention is substantially similar to the operation of the preferred embodiment, except that only the drain segment 131 and the transition tube segment 151 of the catheter are formed with this die.

Material suitable for being formed into the catheter of the present invention is pumped through sprue 215 and into the plenum contained in the main body 212. Within the plenum the pressure of the material is equalized and the material flows through opening 239 in the main body 212 and directly through die cavity 223. When the first die form 243 is in its first position in the die cavity, the drain tube segment 131 is formed with the curved portions of die mandrel 263 forming channels 136 and the prongs of die form 243 creating grooves 135 (FIG. 6b).

By moving the first die form 243 to its second position, withdrawn from the die cavity 223, the transition tube segment 151 of the drain is formed. After a length of alternating drain and transition tube segments has been formed, the extruded tube is cut into segments, each of which contains a drain segment and a transition tube segment. The free end of the transition tube segment 151 is connected in an abutting relationship with a length of extension tubing 173, as shown in longitudinal cross section in FIG. 21. The length of extension tubing is a tubular body with a central longitudinal cavity. This central cavity communicates with all of the channels of the transition tube segment 151. A collar 184 is fitted around the outer surface of the end of the transition tube segment 151 and the outer surface of the end of the extension tubeing 173.

Use of the catheter so formed is identical to the use of the preferred embodiment of the catheter of the present invention described above. Even though the extension tube 173 is not formed as part of a single elongate member with the transition tube segment and the drain segment, this joint is ordinarily not within the body when the drain is to be removed, so the same advantages of removal are present as with the preferred embodiment.

Second Alternative Embodiment

The die form and die mandrel of a second alternative embodiment of the die of the present invention are shown in FIG. 13. The die nozzle 321 and die cavity 323 into which this die form and die mandrel fit are identical to the die nozzle 21 and die cavity 23 of the first embodiment.

The drain tube catheter extruded by this embodiment of the die is shown in FIG. 16. The wound drain catheter extruded by this second alternate embodiment of the die includes a drain segment 132, shown in cross-section in FIG. 14b. This drain segment 132 is composed of a longitudinal core portion 134 with two outer curved portions 138 surrounding somewhat less than the circumference of the core portion 134. Between these outer portions 138 around the perimeter of the drain segment are flutes or lumens 139.

The drain tube segment 132 is formed with prongs 44 of the first die form in a first position within the die cavity 323 and cylindrical die mandrel 82 withdrawn from the die cavity. In this configuration, the relative positions of the prongs 44 and the cylindrical die mandrel 82 are shown in FIG. 13 and the die nozzle 321 appears as shown in FIG. 14a. The material being extruded flows through die opening 323 in die nozzle 321. Prongs 44 of the first die form create in the extrudate lumens 139, while the parison flows around the prongs 44 to form the central core portion 134 and the curved outer portions 138.

After the drain segment 132 has been formed, the prongs 44 are withdrawn from the die cavity 323 while the cylindrical die mandrel 82 is moved into position in the die cavity 323. For a brief moment during the extrusion process, both the die mandrel 82 and the prongs 44 are within the die cavity 323. At this point in the extrusion process, a transition tube segment 152 is formed, comprising two curved outer portions, similar to portions 138. Located diametrically between these two curved outer portions of the transition tube segment 152 is a longitudinal central cavity, formed by cylindrical die mandrel 82. The gaps around the perimeter of the transition tube segment formed by prongs 44, between the two curved outer portions, form two longitudinal channels similar to the lumens 139 of the drain segment 132. These channels communicate at one end with the lumens 139 and along their lengths with the central cavity of this transition segment. The transition tube segment 152 must be quite short (on the order of a fraction of an inch) so the tube does not collapse when suction is applied to the drain.

After the prongs 44 are removed from the die cavity, and the cylindrical shaft 82 is within the die cavity, the extension tube segment 172 of the drain, shown in cross-section in FIG. 15b, is formed. This extension tube segment 172 includes a tubular body 178 defining a longitudinal central cavity 176. Central cavity 176 communicates at one end with the central cavity of the transition tube segment 152. During this portion of the extrusion process, the die nozzle 321 looks as shown in FIG. 15a. Cylindrical shaft or die mandrel 82 is positioned centrally within die cavity or opening 323 of die nozzle 321 so the extruded material flows around it to form tubular extension tube segment 172.

Third Alternate Embodiment

Yet another embodiment of the die and drain of the present invention is shown in FIGS. 17-20. The drain of this embodiment is shown in FIG. 20. It includes a drain segment 144, shown in cross-section in FIG. 18b. The drain segment 144 has a substantially cylindrical shape, but has a groove in its outer surface to define one lumen 148 which is open to the environment.

The extension tube segment 174 of this embodiment, shown in cross-section in FIG. 19b, comprises a substantially tubular body 179 defining a central longitudinal cavity 186. Between the extension tube segment 174 and the drain segment 144 is a transition tube segment of very short length, comprising a substantially tubular body having an enclosed longitudinal channel that communicates at one end with the longitudinal lumen 148 of the drain segment and at the other end with the longitudinal cavity 186 of the extension tube segment.

The die used to form this third alternate embodiment of the drain of the present invention includes a die mandrel 84 asymmetrically mounted on the end of a rotatable shaft 94, shown in FIG. 17a. Rotation of shaft 94 moves die mandrel 84 from a position adjacent the edge of die opening 423, shown in FIG. 17b, to a position substantially in the center of die opening 423, as shown in FIG. 17c.

When the shaft 94 and die mandrel 84 are in the first position, with die mandrel 84 adjacent the edge of die opening 423, the drain segment 144 is formed. Die mandrel 84 forms in the extrudate flowing through die cavity 423 lumen 148, as shown in FIGS. 18a and 18b.

As shaft 94 is rotated while the extrusion process continues, the die mandrel 84 rotates away from the edge of die cavity 423 and toward the center of the die opening 423. As the die mandrel 84 moves in this way it forms the internal channel of the transition tube segment. The rotation of shaft 94 is stopped when the die mandrel 84 is in approximately the center of the die opening 423.

With the die mandrel 84 positioned in the center of die opening 423, as shown in FIG. 19a, the tubular extension tube segment 174 is formed by the extrusion process.

Use of Second and Third Alternate Embodiments

The two embodiments of the catheters described immediately above, providing only one or two lumens, are capable of being made to substantially smaller dimensions than the drains providing multiple lumens of the first two embodiments. These smaller drains are advantageous for use in smaller wounds that do not need a large amount of fluid drainage. The method of using the alternate embodiments of the catheter is the same as the method of using the preferred embodiment.

The dies from which the catheters of the second and third alternate embodiments are extruded may also include two or more plenums similar to second and third plenums 25 and 29 of the preferred embodiment of the die, so the alternate embodiments of the catheters can be formed partially of radiopaque material and partially of translucent material.

Other Uses

The drains of the present invention may also be advantageously used to drain fluid from or supply fluid to environments other than closed deep wounds. The dies of the present invention, incorporating die forms and die mandrels that are movable within the die cavity during the extrusion process, may also be used advantageously to form other extruded products having cross sections that are not uniform throughout their length.

What is claimed is:

1. An elongate catheter of one piece construction for draining fluid from or supplying fluid to an environment comprising:
   a drain segment of substantially constant cross section throughout its length having plural elongate fluid openings in the form of grooves extending throughout the length of the sidewall thereof, said openings spaced circumferentially from one another;
   a second transition segment with closed sidewalls in fluid communication with said elongate openings of said drain segment, having an perimeter size, in cross section, substantially the same as that of said drain segment, but having an interior cross section different from that of said drain segment.

2. A catheter, as defined in claim 1, wherein said drain segment of said elongate catheter comprises:
   a core portion having a longitudinal axis; and plural T-shaped members projecting therefrom to define between said T-shaped members said plural fluid openings.

3. A catheter, as defined in claim 1, wherein said second transition segment of said elongate catheter comprises:
   a core portion having a longitudinal axis;
   plural strut portions projecting from said core portion; and
   a tubular portion connected on its inner surface to the outer ends of said plural strut portions to define plural longitudinal lumens.

4. The catheter defined in claim 1, wherein:
   a first fraction of said elongate catheter is formed of radiopaque material; and
   a second fraction of said elongate catheter is formed of translucent material.

5. The catheter defined in claim 4, wherein:
   said first fraction comprises a portion of said drain segment of said elongate member; and
   said second fraction comprises a portion of said second segment of said elongate member.

6. A catheter, as defined in claim 1, wherein said drain segment of said elongate catheter comprises:
   a central core portion; and
   plural curved outer portions, said outer portions fitting around, and connecting with, a substantial portion, but less than all, of the circumference of the outer surface of said core portion, a gap between the edges of said outer portions defining said fluid openings.

7. A catheter, as defined in claim 6, wherein said second segment comprises:
   a first length of said elongate catheter comprising:
   a cylindrical outer wall surrounding plural longitudinal channels, said channels communicating with said fluid openings of said drain segment.

8. A catheter, as defined in claim 7, wherein said second segment additionally comprises:
   a second length of said elongate catheter comprising a tubular portion having a single central longitudinal cavity, said cavity in communication with said plural longitudinal channels of said first length.

9. A catheter, as defined in claim 1, wherein said unitary elongate catheter additionally comprises a third segment in fluid communication with said second segment and having a different cross section from said second segment.

10. A catheter, as defined in claim 9, wherein said third segment comprises:
a third length of said elongate catheter comprising a tubular portion having a single central longitudinal cavity, said cavity communicating with said second segment.

11. A catheter, as defined in claim 1, wherein said unitary elongate catheter is formed of a flexible silicone material.

12. A catheter, as defined in claim 1, wherein said unitary elongate catheter is formed of a material having a durometer shore of from 40 to 70 shore A.

13. A method of drawing fluid from, or supplying medication to, a wound, comprising:
providing a unitary elongate resilient elastomeric member having a constant outside diameter, said member comprising:
a drain segment; and
a second transition segment with closed sidewalls in fluid communication with said drain segment having a different cross section from said drain segment;
placing said drain segment and at least a portion of said second transition segment in said wound;
connecting said second segment to a fluid reservoir; and
removing said drain segment from said wound by applying a tensile force to said elongate member, causing said drain segment and said second transition segment portion to decrease in cross sectional area to reduce the gripping force of the tissue surrounding the member.

14. The method defined in claim 13, additionally comprising the step of closing said wound after placing said drain segment in said wound to seal said wound from the atmosphere.

* * * * *